(12) United States Patent
Paul, Jr.

(10) Patent No.: US 9,918,824 B2
(45) Date of Patent: Mar. 20, 2018

(54) BLOOD PERFUSION DEVICE DELIVERY SYSTEM

(71) Applicant: Cook Medical Technologies LLC, Bloomington, IN (US)

(72) Inventor: Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 659 days.

(21) Appl. No.: 14/324,878

(22) Filed: Jul. 7, 2014

(65) Prior Publication Data

US 2014/0324155 A1 Oct. 30, 2014

Related U.S. Application Data

(62) Division of application No. 13/197,074, filed on Aug. 3, 2011, now abandoned.

(Continued)

(51) Int. Cl.
*A61F 2/06* (2013.01)
*A61F 2/07* (2013.01)
(Continued)

(52) U.S. Cl.
CPC .................. *A61F 2/07* (2013.01); *A61F 2/06* (2013.01); *A61F 2/848* (2013.01); *A61F 2/86* (2013.01);
(Continued)

(58) Field of Classification Search
CPC .... A61F 2/064; A61F 2/07; A61F 2/86; A61F 2/90; A61F 2/962; A61F 2/97; A61F 2002/061; A61F 2002/072; A61F 2002/075; A61F 2210/0004; A61F 2310/00389; A61F 2250/0031; A61F 2250/003; A61F 2/82;
(Continued)

(56) References Cited

U.S. PATENT DOCUMENTS 4,442,837 A 4/1984 Keatley
4,743,265 A 5/1988 Whitehouse et al.
(Continued)

FOREIGN PATENT DOCUMENTS

WO WO 2005/048880 A2 6/2005
WO WO 2008/138529 A1 11/2008

*Primary Examiner* — Jonathan Miles
*Assistant Examiner* — Kendra Obu
(74) *Attorney, Agent, or Firm* — Brinks Gilson & Lione (57) ABSTRACT

A delivery system deploys a prosthesis for open surgical repair of a body vessel. The system includes a sleeve to retain segments of a prosthesis in a compressed configuration and retraction members. The sleeve has outer segments associated with each end of the prosthesis. Retraction of the retraction members removes the outer segments of the sleeve from the prosthesis outer ends to allow for expansion of the outer ends of the prosthesis in an outside-in direction. The system can include a handle and an actuation member movably attached to the handle. The actuation member is coupled to the sleeve outer segments so that movement of the actuation member corresponds to removal of the sleeve. The system can include elements to retain the sleeve outer segments to the actuation member and to redirect the retraction members to a direction different from the axis of the prosthesis.

33 Claims, 6 Drawing Sheets

Related U.S. Application Data (60) Provisional application No. 61/370,304, filed on Aug. 3, 2010.

(51) Int. Cl.
| | | |
|---|---|---|
| *A61F 2/915* | (2013.01) | |
| *A61F 2/86* | (2013.01) | |
| *A61F 2/848* | (2013.01) | |
| *A61F 2/89* | (2013.01) | |
| *A61B 17/11* | (2006.01) | |

(52) U.S. Cl.
CPC ....... *A61F 2/915* (2013.01); *A61B 2017/1107* (2013.01); *A61B 2017/1132* (2013.01); *A61F 2/89* (2013.01); *A61F 2002/075* (2013.01); *A61F 2002/8483* (2013.01); *A61F 2002/91558* (2013.01); *A61F 2002/91575* (2013.01); *A61F 2210/0076* (2013.01); *A61F 2220/005* (2013.01); *A61F 2220/0058* (2013.01); *A61F 2220/0066* (2013.01); *A61F 2220/0075* (2013.01); *A61F 2250/0023* (2013.01); *A61F 2250/0036* (2013.01); *A61F 2250/0037* (2013.01)

(58) Field of Classification Search
CPC .......... A61F 2/844; A61F 2/848; A61F 2/852; A61F 2/856; A61F 2/91; A61F 2/885; A61F 2/89; A61F 2/915; A61F 2/92; A61F 2/93; A61F 2/94; A61F 2/95; A61F 2/954; A61F 2/958; A61F 2/966; A61F 2/2418; A61F 2/2427; A61F 2/243; A61F 2/2436; A61F 2/2439; A61F 2/2466; A61F 2002/821; A61F 2002/823; A61F 2002/825; A61F 2002/826; A61F 2002/828; A61F 2002/8483; A61F 2002/8486; A61F 2002/91508; A61F 2002/91516; A61F 2002/91525; A61F 2002/91533; A61F 2002/91541; A61F 2002/9155; A61F 2002/91558; A61F 2002/91566; A61F 2002/91575; A61F 2002/91583; A61F 2002/91591; A61F 2002/9505; A61F 2002/9511; A61F 2002/9517; A61F 2002/9522; A61F 2002/9528; A61F 2002/9534; A61F 2002/9583; A61F 2002/9586; A61F 2002/9665; A61F 2210/0042; A61F 2210/0061; A61F 2210/0066; A61F 2210/0071; A61F 2210/0076; A61F 2240/001; A61F 2240/002; A61F 2310/00796; A61F 2250/001; A61F 2250/0012; A61F 2250/0023; A61F 2250/0024; A61F 2250/0046; A61F 2250/0056; A61F 2250/0058; A61F 2250/0059; A61F 2250/0069; A61F 2250/0071; A61F 2250/0067

See application file for complete search history.

(56) References Cited

U.S. PATENT DOCUMENTS

| | | |
|---|---|---|
| 5,591,226 A | 1/1997 | Trerotola et al. |
| 5,830,217 A * | 11/1998 | Ryan ..................... A61F 2/91 623/1.11 |
| 6,254,628 B1 | 7/2001 | Wallace et al. |
| 6,562,048 B1 | 5/2003 | Fogarty et al. |
| 7,960,453 B2 | 6/2011 | Heinzman et al. |
| 8,388,634 B2 | 3/2013 | Osypka Rubenstein et al. |
| 2007/0027526 A1 | 2/2007 | Demetriades et al. |
| 2007/0198077 A1 | 8/2007 | Cully et al. |
| 2009/0112237 A1 | 4/2009 | Paul, Jr. et al. |
| 2009/0204196 A1 | 8/2009 | Weber |
| 2010/0168837 A1 | 7/2010 | Magnuson et al. |
| 2010/0324653 A1 | 12/2010 | Rubenstein et al. |
| 2012/0165915 A1 * | 6/2012 | Melsheimer ............ A61F 2/064 623/1.11 |

* cited by examiner

BLOOD PERFUSION DEVICE DELIVERY SYSTEM

CROSS-REFERENCE TO RELATED APPLICATIONS

This application is a divisional of U.S. patent application Ser. No. 13/197,074, filed Aug. 3, 2011, which claims the benefit of U.S. Provisional Application No. 61/370,304, filed Aug. 3, 2010, both of which are incorporated herein by reference in their entirety.

BACKGROUND

The preferred embodiments described herein relate generally to medical device delivery systems for open surgical repair of body structures that define body lumens. More particularly, they relate to medical device delivery systems for repairing damaged body structures and gaining hemostasis or fluid stability during emergency open surgical medical procedures.

Trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by trauma physicians to treat body vessel injuries include the clamping of the vessel with a hemostat, the use of a balloon tamponade, the ligation of the damaged vessel at or near the site of injury, or the insertion of one or more temporary shunts. However, conventional surgical repair is generally difficult with such actively bleeding, moribund patients. In many instances, there is simply not enough time to repair the body vessel adequately by re-approximating and suturing the body vessel. In many situations, the trauma physician will simply insert a temporary shunt (such as a Pruitt-Inahara Shunt) into the vessel. However, use of temporary shunts has been linked to the formation of clots. This may require returning the patient to the operating room for treatment and removal of the clots, often within about 36 to 48 hours of the original repair. Since shunts are generally placed as a temporary measure to restore blood flow and stop excessive blood loss, the shunt is typically removed when the patient has stabilized (generally a few days later) by a specialized vascular surgeon. After removal, the vascular surgeon will replace the shunt with a vascular graft, such as a fabric graft that is sewn into place. With respect to ligation, ligation of the damaged blood vessel may result in muscle necrosis, loss of muscle function, or a potential limb loss or death.

Due to the nature of the body vessel injury that may be encountered, the insertion of shunts or ligation of a blood vessel, for example, often requires that such treatments be rapidly performed at great speed, and with a high degree of physician skill. Such treatments may occupy an undue amount of time and attention of the trauma physician at a time when other pressing issues regarding the patient's treatment require immediate attention. In addition, the level of particularized skill required to address a vascular trauma may exceed that possessed by the typical trauma physician. In particular, traumatic episodes to the vessel may require the skills of a physician specially trained to address the particular vascular trauma, and to stabilize the patient in the best manner possible under the circumstances of the case.

Some open surgical techniques utilize sutures to affix damaged tissue portions surrounding fittings that have been deployed with the vessel, which requires the trauma physician to take time to tie the sutures properly. Although in modern medicine sutures can be tied in relatively rapid fashion, any step in a repair process that occupies physician time in an emergency situation is potentially problematic. In addition, the use of sutures to affix the vessel to the fitting compresses the tissue of the vessel against the fitting. Compression of tissue may increase the risk of necrosis of the portion of the vessel tissue on the side of the suture remote from the blood supply. When present, necrosis of this portion of the vessel tissue may result in the tissue separating at the point of the sutures. In this event, the connection between the vessel and the fitting may eventually become weakened and subject to failure. If the connection fails, the device may disengage from the vessel. Therefore, efforts continue to develop techniques that reduce the physician time required for such techniques, so that this time can be spent on other potentially life-saving measures, and the blood flow is more quickly restored and damage caused by lack of blood flow is minimized.

Trauma physicians generally find it difficult to manipulate a prosthesis for insertion into a body vessel that has been traumatically injured. For example, one difficulty arises from the trauma physician trying to limit the size of the opening created for gaining access to the injured vessel so that such opening requiring healing is as small as possible. Another difficulty is that the injured vessel can be anywhere in the body, having different surrounding environments of bone structure, muscle tissue, blood vessels, and the like, which makes such obstructions difficult to predict in every situation and leaves the trauma physician working with an even further limited access opening. Another potential consideration is the amount of body vessel removed during a transection. The goal would be to remove a portion of the body vessel as small as possible. Yet, a small portion removed from the vessel leaves such a small space between the two vessel portions, thereby making it difficult to introduce the prosthesis between the two vessel portions.

Thus, what is needed is a delivery device for delivering a prosthesis for use in repair of an injured body vessel, such as an artery or a vein, (and in particular a transected vessel) during emergency open surgery. It would be desirable if such delivery device was easy for a trauma physician to use, and can rapidly introduce a prosthesis into a body vessel, thereby providing a conduit for blood or fluid within the injured body vessel.

SUMMARY

The problems of the prior art are addressed by the features of the following examples. In one aspect, a delivery system can include a sleeve and first and second retraction members. The sleeve can be configured to retain segments of a prosthesis in a compressed configuration. The sleeve can have a first outer segment and a second outer segment associated with a first outer end and a second outer end of the prosthesis, respectively. The first retraction member can be coupled to the first outer segment of the sleeve, and the second retraction member can be coupled to the second outer segment of the sleeve. In response to retraction of the first and second retraction members, the first and second outer segments of the sleeve are removed from the corresponding outer ends of the prosthesis. Such removal allows for the expansion of the outer ends of the prosthesis in an outside-in direction.

In another aspect, the delivery system can include a handle and an actuation member movably attached to the handle. An assembly can be disposed at a distal end of the handle. The assembly can include a sleeve configured to retain segments of a prosthesis in a compressed configuration. The sleeve can have a first outer segment and a second outer segment that are associated with a first outer end and a second outer end of the prosthesis, respectively. A first retraction member can be coupled between the first outer segment of the sleeve and the actuation member, and a second retraction member can be coupled between the second outer segment of the sleeve and the actuation member. In response to movement of the actuation member relative to the prosthesis from a first position to a second position, the first and second outer segments of the sleeve are removed from the corresponding outer ends of the prosthesis. This removal allows for the expansion of the outer ends of the prosthesis in an outside-in direction. The handle may include a guiding member to redirect the retraction members from a direction generally along the longitudinal axis to a direction different from the longitudinal axis, such as along the translational axis of the actuation member, which is generally perpendicular to the longitudinal axis. The actuation member may include a retaining member configured to removably attach with each of the retraction members.

Further, in another aspect, a method of open surgical repair of a body vessel is provided. The method can include one or more of the following steps, including inserting a first outer end of a prosthesis in a first vessel portion of a body vessel. The first outer end of the prosthesis can be retained in a compressed configuration by a sleeve portion. A second outer end of the prosthesis can be inserted in a second vessel portion. The second outer end of the prosthesis can be retained in a compressed configuration by a sleeve portion. The sleeve portions can be composed of a single sleeve or multiple sleeves. Sleeve portions can be removed from the respective first and second outer ends of the prosthesis. The first and second outer ends of the prosthesis can be allowed to move to an expanded configuration for engagement with the corresponding vessel portion of the body vessel. In one example, the sleeve portions can be removed with application of an activation agent configured to rapidly weaken or to dissolve the sleeve portions.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. Throughout the specification, when referring to a medical device, or a portion of a medical device, the terms "distal" and "distally" shall denote a position, direction, or orientation that is generally towards, or in the direction of, the patient when the device is in use. The terms "proximal" and "proximally" shall denote a position, direction, or orientation that is generally away from the patient, or closer to the operator, during use of the device. It is understood that like-referenced numerals are used throughout the Figures to designate similar components.

The delivery system described herein can deploy a prosthesis that is useful for repair of body structures that define lumens, ducts, or passageways of the body, with the term "body vessel" used in the specification to describe theses structures in general, during emergency open surgical repair. In one example, the prosthesis can be particularly useful for repair of a lacerated or transected body vessel during emergency open surgery, and particularly, to obtain hemostasis or fluid stability while maintaining blood perfusion or fluid flow. While some prosthetic devices are only implanted temporarily for treatment, the prosthesis can be implanted permanently thereby obviating the need for further surgical intervention and repair. In one application with respect to a blood vessel, blood vessels are of two types, namely arteries and veins. Generally speaking, arteries are elastic vessels that carry oxygenated blood away from the heart, and veins are elastic vessels that transport blood to the heart and that then transport blood to the lungs for oxygenation. The walls of both arteries and veins generally consist of three layers or tunics. The inner layer is referred to as the tunica intima, which is composed of endothelium and delicate collagenous tissue. The middle layer is referred to as the tunica media, which is composed of typically a muscular layer, and consists of smooth muscle and elastic fibers. The outer layer is referred to as the tunica adventitia, which is the outer covering of the vessel, and is composed of connective tissue, collagen, and elastic fibers. The tunic adventitia includes small vessels, referred to as vasa vasorum, which supply nutrients to the tissue. Preferably, the prosthesis controllably interacts with the tunica intima, basement membrane, and tunica media, and avoids interaction with the tunica adventitia to not disrupt the vasa vasorum residing in the tunica adventitia. The prosthesis can be secured in a rapid manner without the use of a ligature or suture placed around the vessel.

Figure 1A:
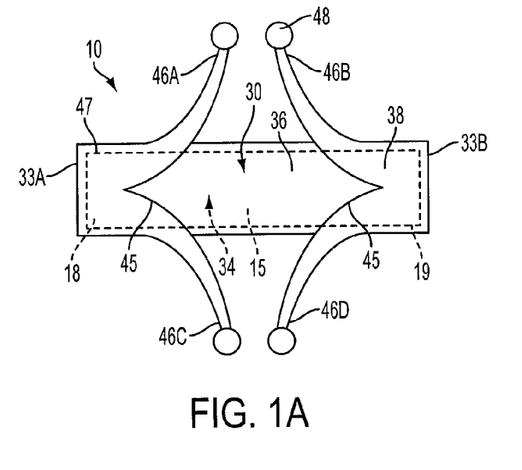
FIG. 1A is an elevation view of an example delivery system having a prosthesis retained in a compressed configuration by a removable sleeve.
Figure 1B:
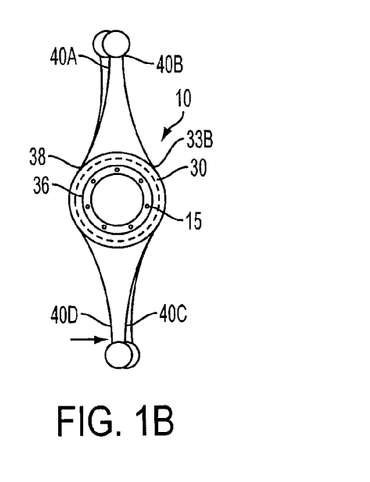
FIG. 1B is an end view of the system of FIG. 1A.

FIGS. 1A-1B depict one example delivery system 10 including a prosthesis 15 (shown in dashed lines) retained in a radially compressed configuration by a removable tubular sleeve 30. The removable sleeve 30 may be fitted at least partially over the first and/or second outer ends 18, 19 of the prosthesis 15 to selectively retain the outer ends in the compressed configuration for insertion into an end opening of the a vessel. As shown in the figures, the removable sleeve 30 may be composed of a single sleeve configured to retain the entire prosthesis from the first end 18 to the second end 19 of the prosthesis 15. In another example, the removable sleeve 30 may include two discrete sleeve portions (not shown). Here, the removable sleeve includes a first sleeve portion retaining a first outer segment of the prosthesis 15 associated with the first outer end 18, and a second sleeve portion retaining a second outer segment of the prosthesis 15 associated with the second outer end 19, leaving an intermediate segment between the first and second outer segments unretained by the removable sleeve.

The removable sleeve 30 can be everted or folded at a point of eversion 33A, 33B proximate the outer ends 18, 19 of the prosthesis 15 and be directed toward a middle 34 of the prosthesis. This arrangement can form a radially inner layer 36 and a radially outer layer 38 of the sleeve 30 and allows the ends of the outer layer to gather toward the prosthesis middle 34. In one example, the outer layer 38 and the inner layer 36 are two separate tubular members that are coupled to one another by an attachment mechanism, such as by adhesives, soldering, welding, sewing or other common attachment mechanisms. The inner layer 36 can directly contact the prosthesis 15 to extend along at least partially a segment of the prosthesis. The outer layer 38 can extend from the outer end of the inner layer 36 to a more intermediate portion of the inner layer. The inner and outer layers may slidably interact with one another during retraction of the outer layer ends. To this end, a lubricious coating may be applied to suitable portions of the layers to facilitate their interaction. The lubricious coating can be a fluoropolymer of the type commonly used to impart lubricity to a medical device, and most preferably, polytetrafluoroethylene (PTFE).

In one example, the sleeve 30 may be pre-split in order to facilitate mechanical removal of the sleeve from the prosthesis. In a pre-split sleeve, any number of splits 45 can be pre-formed in the outer layer from the outer layer end toward an intermediate portion proximate the eversion points 33A, 33B. Having a solid outer layer material between the eversion point and the beginning of the split forms a sold ring 47 of material around the ends of the prosthesis, which preferably overlays the anchoring members of the prosthesis. The solid ring 47 can comprise the outer layer and the inner layer together forming a double layer of materials to enhance the retention of the outer ends of the prosthesis to the compressed configuration.

The outer layer and its ends can be manipulated and retracted by the end user to remove the sleeve from the prosthesis. To this end, the system can include at least two retraction members associated with the outer ends of the prosthesis. The first and second retraction members can be independently retractable. FIG. 1A shows four splits that form the four outer layer ends, although two or three or more outer layer ends may be formed. The four outer layer ends can define first and third retraction members 46A, 46C associated with the first outer end 18 of the prosthesis 15 and second and fourth retraction members 46B, 46D associated with the second outer end 19 of the prosthesis 15. The ends of the retraction members can be enlarged or have an enlarged knob 48 attached thereto to facilitate gripping and manipulation of the sleeve 30 during removal from the prosthesis. The retraction member is operable for peeling and/or splitting the sleeve 30 from the respective outer ends 18, 19 toward the middle 34 of the prosthesis 15 to allow for expansion thereof. In one example, the retraction member and the removable sleeve are formed integrally from a single tubular piece of sleeve material. Here, the outer end of the tubular sleeve is everted along the prosthesis so that the everted portions form the retraction member. Alternatively, the retraction member may be a discrete member from the sleeve. Here, the retraction member may be composed of sleeve material and/or a tension member, such as a wire or a filament of biocompatible metal or plastic. The discrete retraction member can have a first end attached to the outer end of the removable sleeve and a second end that is accessible by the end user.

A concise description of the prosthesis 15 will now be provided. One example of a prosthesis is described in U.S. patent application Ser. No. 13/197,511, filed on Aug. 3, 2011, entitled "BLOOD PERFUSION DEVICE," which is incorporated herein by reference in its entirety. The prosthesis 15 can include a generally tubular graft body and/or one or more anchoring members 49 and/or supporting members together defining a fluid passageway. The prosthesis 15 is movable between the radially compressed, delivery configuration and the radially expanded, deployed configuration. The prosthesis can be balloon expandable; however, it is preferred that the prosthesis is self-expandable. The anchoring members and/or supporting members can be attached to the graft body by sutures sewn therein, wire, staples, clips, bonding agents, or other methods that may be used to achieve a secure attachment to the graft body. The prosthesis has a size and shape suitable for at least partial placement within a body vessel, such as an artery or vein, and most particularly, for placement at the site of a vascular trauma. The prosthesis may be easily manipulated during delivery to a body vessel such as a transected artery or vein during emergency surgery, and particularly, to obtain hemostasis while maintaining blood perfusion. The anchoring member and/or supporting member can be any stent pattern known to one skilled in the art. Examples of stent patterns is the Z-STENT® and ZILVER® stent, each available from Cook Medical Inc. (Bloomington, Ind.). The anchoring member and/or supporting member can be formed of a biocompatible metal, such as stainless steel (e.g., 316L SS), titanium, tantalum, nitinol or other shape memory materials, or a high-strength polymer. Preferably, the anchoring member 49 can provide vessel fixation, while preferably avoiding adverse conditions associated with disturbing the vasa vasorum and/or pressure induced necrosis of the medium muscular arteries of the type that may result from tying ligatures circumferentially around a connector or a vascular conduit. The anchoring member 49 can include various shaped member structures, including barbs, fibers, bristles, or outer protruding and penetrable media.

The graft body can be formed from conventional materials well known in the medical arts. The graft body may comprise an expanded polytetrafluoroethylene (ePTFE), polytetrafluoroethylene, silicone, polyurethane, polyamide (nylon), as well as other flexible biocompatible materials. The graft body can also be formed from known fabric graft materials such as woven polyester (e.g. DACRON®), polyetherurethanes such as THORALON® from Thoratec Corporation (Pleasanton, Calif.), polyethylene such as an ultra-high molecular weight polyethylene (UHMwPE), commercially available as DYNEEMA®. The graft body may also include a bioremodelable material, such as reconstituted or naturally-derived collagenous materials, extracellular matrix material (ECM), submucosa, renal capsule membrane, dermal collagen, dura mater, pericardium, fascia lata, serosa, peritoneum or basement membrane layers, intestinal submucosa, including small intestinal submucosa (SIS), stomach submucosa, urinary bladder submucosa, and uterine submucosa. One non-limiting example of a suitable remodelable material is the SURGISIS® BIODESIGN™, commercially available from Cook Medical Inc. (Bloomington, Ind.). Another suitable remodelable material is the graft prosthesis material described in U.S. Pat. No. 6,206,931 to Cook et al., which is incorporated herein by reference in its entirety.

Portions of the prosthesis can also include a coating of one or more therapeutic agents along a portion of the stent structure and/or the graft body. Therapeutic agents for use as biocompatible coatings are well known in the art. Non-limiting examples of suitable bioactive agents that may be applied to the vascular conduit include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Those skilled in the art will appreciate that other bioactive agents may be applied for a particular use. The bioactive agent can be incorporated into, or otherwise applied to, portions of the vascular conduit by any suitable method that permits adequate retention of the agent material and the effectiveness thereof for its intended purpose. Although the device has been described in connection with its primary intended use for repair of vascular trauma, those skilled in the art will appreciate that the device may also be used to repair other traumatic conditions. Non-limiting examples of such conditions include aneurysms, such as abdominal aorta aneurysms, and surgery for tumor removal.

The sleeve 30 can be made of any material that is biocompatible and suitable to retain the prosthesis in the radially compressed configured and yet still capable of being peeled from the prosthesis and/or split. It is desirable that the sleeve is made from materials that are thin as possible to reduce the overall delivery profile of the system. For example, the sleeve can be extruded from a biocompatible polymer material. In addition, the sleeve can be formed of at least one layer such as a polyether block amide, nylon, polyurethane, polytetrafluoroethylene (PTFE), FEP, or any combination thereof. In one example, the sleeve can be removed from the prosthesis without splitting. In another example, the sleeve can be configured to be separated, preferably longitudinally, along a relatively predictable path. The material of the sleeve is configured to be split or cut into two or more portions by movement of the sleeve alone relative to the prosthesis and/or movement of the sleeve against a handle portion, thereby opening a fissure along the length that permits its removal from around the prosthesis situated therein. A predetermined split line may be formed in the sleeve through which the tear or split progresses due to properties of, and/or features incorporated into the material. When present, the predetermined split line can withstand being subjected to a curve to the degree required by the particular application without kinking or premature separation. In one example, the sleeve can comprise a splittable polymer such as molecularly oriented, non-isotropic PTFE that is used to make the PEEL-AWAY® Introducer Sheath, which is commercially provided by Cook Medical Inc. (Bloomington, Ind.). Such sleeve is described in, e.g., U.S. Pat. No. 4,306,562 to Osborne and U.S. Pat. No. 4,581,025 to Timmermans, each of which is incorporated herein by reference in its entirety. In other examples, the sleeve can include one or more preweakened features, such as a score line, perforations, or reduced wall thickness regions, extending longitudinally along the length of the sleeve.

Figure 2A:
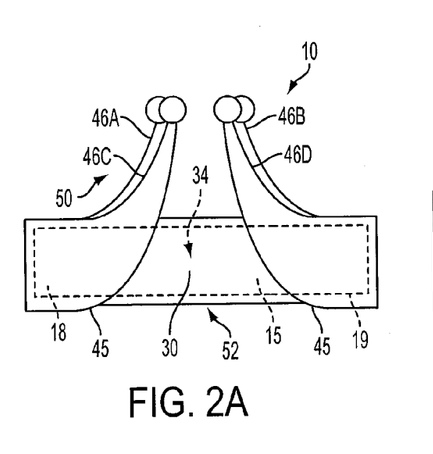
FIGS. 2A-2B are elevation views of the system FIG. 1A, depicting operation of the system for removal of the sleeve from the prosthesis.
Figure 2B:
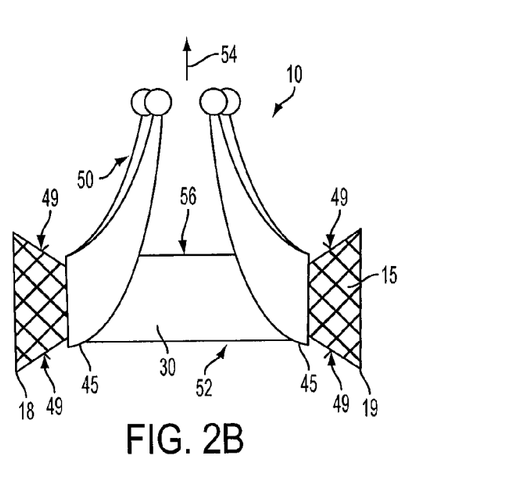

FIGS. 2A-2B show an example method of removing the sleeve 30 from the prosthesis 15 in order to allow the prosthesis to radially expand. In FIG. 2A, the delivery system 10 can be reoriented such that the retraction members 46A-46D are gathered toward the prosthesis middle 34 at a single side 50 of the system 10. This arrangement places some of the splits 45 on another side 52, opposite the side 50. Typically, a trauma pathway is formed in the body in order to gain access to the desired body vessel. One or both ends 18, 19 of the prosthesis retained by the sleeve can be inserted within the body vessel, as described below. According to FIG. 2B, the retraction members 46A-46D can be moved relative to the side 52, in a radial direction represented by arrow 54 within the trauma pathway, to cause a portion of the sleeve 30 to further peel or separate the splits 45 (i.e., increase the length of the splits). This action removes a portion of the sleeve 30 away from the outer ends 18, 19 from an outside-in direction in order to allow for radial expansion of the prosthesis 15 at its ends 18, 19, where the anchor members 49 can engage the body vessel wall. The sleeve 30 can be first removed along the surface of the prosthesis in the outside-in direction along the outer surface of the prosthesis initially before being moved in the radial outward direction 54. As can be appreciated by those skilled in the art, the retraction members can be moved relative to the side 52 until the sleeve 30 is entirely removed from the prosthesis. To facilitate removal, a force or a structure 56 can be placed approximately at the prosthesis middle 34 for leverage as the sleeve is being removed. The retraction members are pulled in the retraction direction until the sleeve is entirely removed from the prosthesis. The expansion force of the prosthesis may facilitate the peeling and/or splitting of the sleeve during the removal process.

Figure 3A:
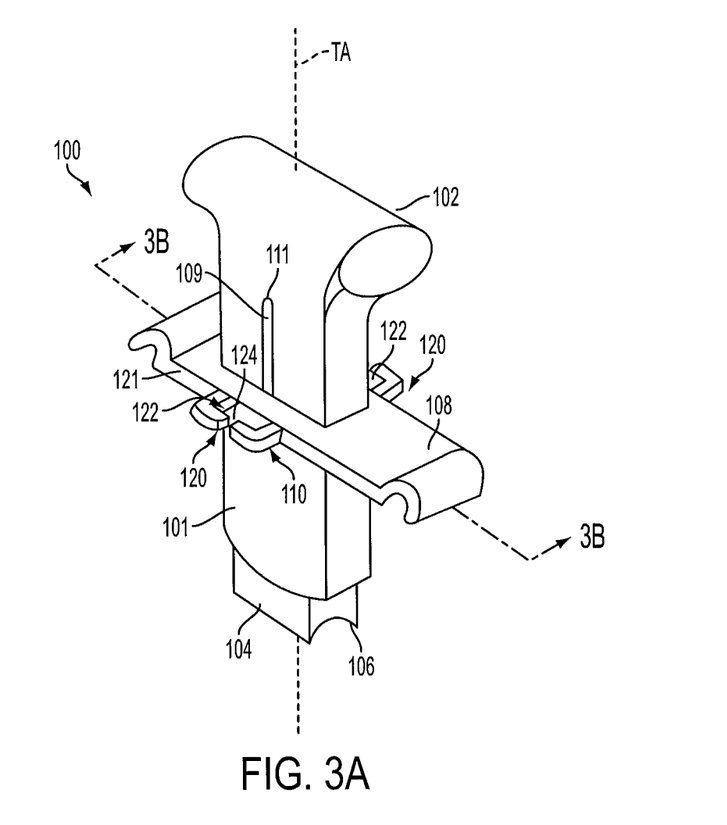
FIG. 3A is a perspective view of an example delivery system, and in particular, a system for use with the delivery system of FIG. 1A.
Figure 5A:
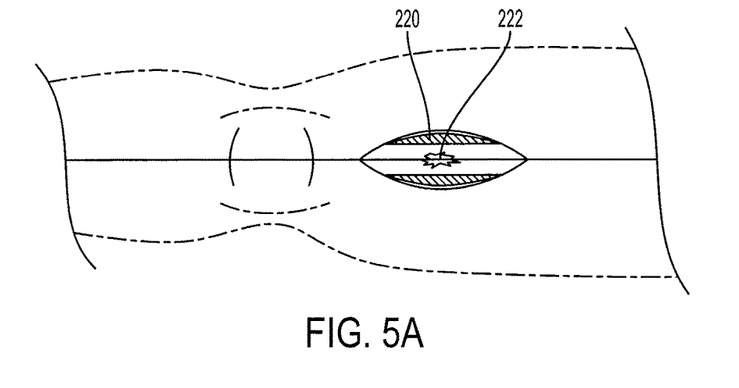
FIGS. 5A-5E illustrate a method of open surgical repair of a body vessel with a delivery system deploying a prosthesis.
Figure 5B:
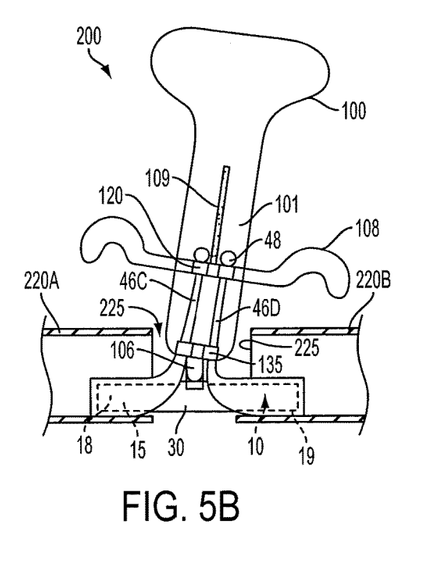

FIG. 3A depicts a delivery tool 100 that may be utilized with the system 10, as will be further explained, to define another delivery system 200, as shown, e.g., in FIG. 5B. The tool 100 can include a handle 101 having a proximal end 102 and a distal end 104. The proximal end 102 can be shaped and sized to fit within a palm of the end user. The distal end 104 can be shaped and sized to engage the system 10 to define the structure 56 in FIG. 2B, e.g., at the prosthesis middle 34. In one example, the distal end 104 may include a contoured tip 106 shaped to fit around the rounded surface of the prosthesis. For example, the tip 106 can have a concave curvature or a saddle shape that is sized to receive the curvature of a portion of the system 10, which includes the sleeve and the prosthesis.

An actuation member 108, such as, e.g., a lever, can be attached to the system handle 101, which can be moved relative to the handle between a first position and a second position along a translation axis TA. The actuation member 108 may be configured to move and cause simultaneous or sequential expansion of the outer ends of the prosthesis. In one example, the actuation members 108 is in the form of a lever shown slidably attached within a slot 109 that is formed approximately through the center of the handle 101. The actuation member 108 may be configured to allow for simultaneous expansion of the outer ends of the prosthesis. However, the actuation member may be configured to allow for sequential expansion of the outer ends of the prosthesis, such as, e.g., having a movable left portion associated with the first outer end and a movable right portion associated with the second outer end. The slot 109 may be an open slot extending entirely through the handle so that access to the open slot is available from opposite sides of the handle. The slot 109 may be a closed slot or a groove formed in opposite sides of the handle, which are not in communication with one another. The slot 109 can provide a guiding channel for the movable actuation member and its ends may function as physical stops to define the first and second positions of the actuation member 108. The slot 109 can be dimensioned so that, when the actuation member 108 is at the first position (e.g., at the distal end 110 of the slot 109), the sleeve 30 can retain the prosthesis in the radially compressed configuration. When the actuation member 108 reaches the second position (e.g., the proximal end 111 of the slot 109), the sleeve 30 can be removed sufficiently to allow at least the outer ends of the prosthesis to expand to the radially expanded configuration. Preferably, when the actuation member 108 reaches the second position, the sleeve 30 can be removed entirely from the prosthesis. The lever 108 may include contoured portions for better receiving the fingers of the end user.

The sleeve 30 can be coupled to the actuation member 108 in such a manner such that movement of the actuation member can change the positioning of the sleeve relative to the prosthesis. For example, the sleeve portions, such as, e.g., the retraction members, can be attached in a secured relationship with the actuation member by a variety of attachment mechanisms, such as clamps, mechanical fasteners, adhesives, welding, soldering, sewing, or attachment mechanisms. The coupling can enhance the removal of the sleeve from the prosthesis. It can also ensure that the retraction member and/or the sleeve remain attached to the tool 100, so that removal of the tool 100 from the body directly corresponds to removal of the retraction member and/or the sleeve from the body as well. Each of the retraction members can be coupled to the first outer segment of the sleeve at a first attachment point and to the actuation member at a second attachment point that is closer in proximity to the middle of the prosthesis.

In one example, the sleeve 30 can be removably attached to the actuation member 108, e.g., by threaded engagement, removable clamps, or mechanical fasteners. For instance, the actuation member 108 can be configured to receive the ends of the retraction members for removable attachment therewith. In one aspect, the actuation member 108 may include a retaining member 120. The retaining member 120 can be attached to the actuation member 108, e.g., to opposite surfaces 121 of the actuation member. The member 120 can include a notch 122 configured to receive a portion of the retraction members. A front opening 124 may be formed in the retaining member that is in communication with the notch 122 to allow the retraction member to pass selectively therethrough.

The retaining member 120 can be a variety of shapes. In one example, the retaining member 120 includes a pair of "L"-shaped elements, having a first leg extending out from the surface 121 of the actuation member 108 and a second leg extending toward the middle. The retaining member 120 can be positioned relative to one another such that the ends of the second legs are spaced from one another to define the front opening 124. It is preferable that the notch 122 and/or the front opening 124 are sized to receive the ends of the retraction members, but sized smaller than the enlarged ends. This arrangement can facilitate the retention of the sleeve and/or the retraction member by the retaining member when the actuation member is moved relative to the prosthesis. The retaining member can cooperatively confine the retraction member into the notch such that the retraction member is prevented from falling out in the direction of the first leg and/or the direction of the second leg. The retaining member 120 can allow for easy attachment and removal of the ends of the retraction members so that the delivery tool 100 can be used and/or reused for a variety of prosthesis sizes. With the ends of the retraction members retained by the actuation member, movement of the actuation member in a proximal direction toward the second position, facilitates relative movement between the sleeve and the prosthesis to cause a portion of the sleeve to further peel or separate the splits.

Figure 3B:
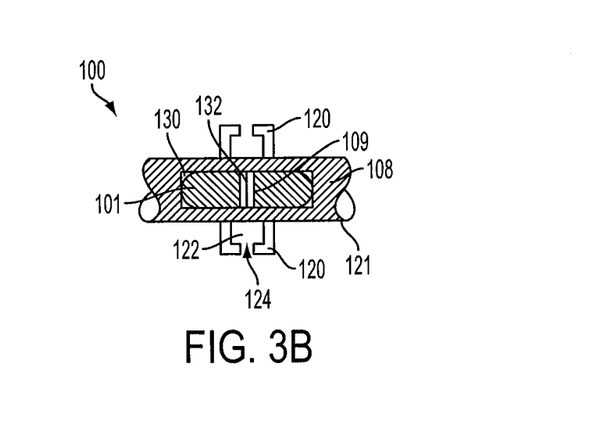
FIG. 3B is a cross-sectional view of the system of FIG. 3A taken along line 3B-3B.

FIG. 3B illustrates that the actuation member 108 may be configured to surround the handle 101. In one example, the actuation member 108 may have a channel 130 formed therein along the translational axis and sized to receive the handle 101. The retaining member 120 can be on either side or both sides of the actuation member 108. A connecting member 132 coupling both sides of the actuation member 108 can be extended through the slot 109. The connecting member 132 can traverse within the slot 109 when the actuation member is being moved between the first position and the second position.

Figure 3C:
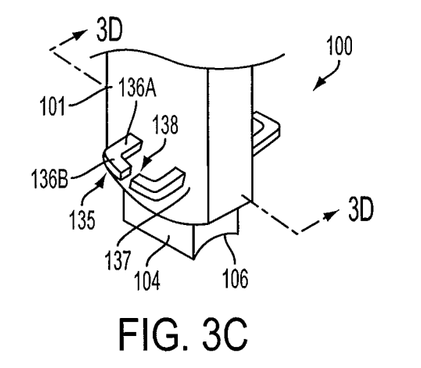
FIG. 3C is a perspective view of a distal end of the system of FIG. 3A, depicting a guiding element.
Figure 3D:
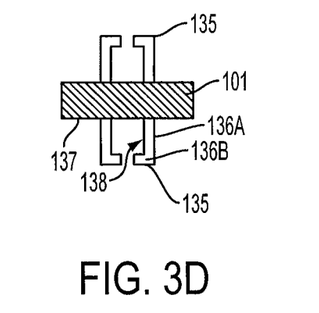
FIG. 3D is a cross-sectional view of the system of FIG. 3C taken along line 3D-3D.

FIGS. 3C-3D illustrate that the tool 100 may include a guiding element 135 that is configured to facilitate the transition of the retraction member from a horizontal direction in the figures, such as along the longitudinal axis of the prosthesis, to a different direction, such as along the translational axis or vertical direction in the figures. The guiding element 135 can be extended away from the surface of the handle 101, and can include a leg 136A at which the retraction member is redirected to the different direction. In other words, the guiding element 135 may provide a leverage point where as the end user pulls in a first direction from the trauma pathway, the sleeve peels and/or splits along the horizontal direction generally perpendicular to the pulling direction. The guiding element 135 can be a variety of shapes, such as an elongate body or "L"-shaped, having the leg 136A extending out from the surface 137 of the handle 101 and a second leg 136B extending toward the middle to define an opening 138. The opening 138 can be configured to allow the retraction member to pass therethrough in order to lead to the retaining member 120. It is preferable that the opening 138 be sized to allow for movement of the retraction member therein. The guiding element can confine the retraction member into the opening such that the retraction member is prevented from falling out in the direction of the first leg and the direction of the second leg. The first legs 136A of a pair of guiding element may be spaced from one another in order to confine the removal of the retraction member and the sleeve to a cross-sectional area less than the area of the laceration or the size of the gap between the vessel portions. This arrangement permits the retraction member and the sleeve to be removed without contacting or rubbing against the edges of the laceration or the body vessel portions to avoid further damage to the vessel.

Figure 4A:
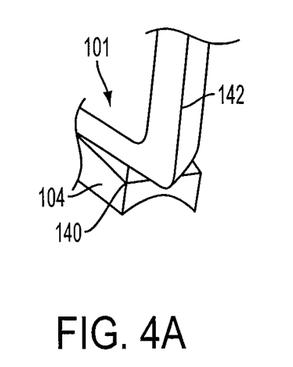
FIG. 4A is a perspective view of a partial distal end of the system of FIG. 3A, depicting a handle body with a sharp edge.
Figure 4B:
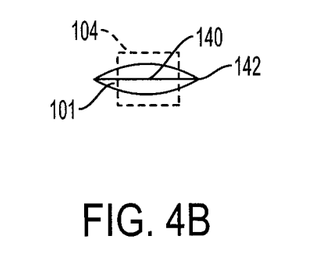
FIG. 4B is an end view of the distal end of the system of FIG. 4A, depicting a sharp edge of the handle body with a distal tip in dashed lines.

FIGS. 4A-4B show another example handle 101, where the distal end of the handle may be configured to facilitate the splitting of the sleeve along the split. In one aspect, the surfaces defining the distal end 104 can converge toward one another to form a first sharp edge 140 along the distal end. In addition to, or instead of, the surfaces of the distal end, the lateral surfaces may converge toward one another to form a second sharp edge 142. When both present, the first and second sharp edges can form a continuous sharp edge. It can be appreciated by those skilled in the art that the edges are sharp enough to facilitate splitting of the sleeve, but not sharp to damage body tissue.

Further appreciation of the tool 100 can be gained with reference to FIGS. 5A-5E, which show the operation of the tool 100 with the system 10 loaded at its distal end to define the delivery system 200. FIG. 5A depicts an example body vessel 220, such as one found in the leg of a patient. The body vessel 220 has previously been subjected to a traumatic episode, resulting in a portion 222 of body vessel 220 being torn away or otherwise severely damaged. Pre-surgery preparation has been applied to the leg and a trauma pathway may be formed therein in order to gain access to the body vessel and the damaged portion thereof. After clamping the body vessel 220 on both ends of the portion 222 to restrict blood flow temporarily, the body vessel 220 can be cut or transected by the clinician into two portions 220A, 220B, as shown in FIG. 5B. In one example, the lacerated portion 222 remains without requiring transection and the opening formed thereby can be used for insertion of the prosthesis. The transection may be at the damaged portion 222 of the blood vessel 220 or as far away as necessary from the damaged portion to remove unhealthy portions of the body vessel or unrepairable portions of the body vessel. Sutures can be attached to the end openings 225 of the body vessel portions 220A, 220B to keep them fixed in place and opened to facilitate insertion of the prosthesis. Forceps may also be used in a similar manner. Any number of sutures can be used to retain the end openings 225 in the open position, although triangulation sutures can be sufficient, with each suture being about 120 degrees apart from the adjacent suture. A prosthesis is selected to have a radial expanded cross-section and a longitudinal length sufficient to bridge the laceration in the vessel or the gap between the body vessel portions 220A, 220B and radially fit within the body vessel portions.

According to FIG. 5B, the delivery assembly 200 is shown inserted into the body through the trauma pathway and positioned at the body vessel. The system 10 with the prosthesis 15 is shown being situated and oriented adjacent the body vessel portions 220A, 220B. The prosthesis 15 is in the delivery, compressed configuration, being at least partially retained in the radially compressed configuration by the sleeve 30. The first outer end 18 of the prosthesis 15 can be inserted into the vessel portion 220A through the end opening 225 by a sufficient distance to allow the anchoring members of the prosthesis to engage within the tissue. It is preferred that the vessel portion initially selected be the non-blood supplying vessel end. The vessel portion 220A may be manually pulled over the first outer end 18 of the prosthesis 15. The actuation member may be configured with at least two portions, where retraction of a first portion of the actuation member is configured to retract the sleeve portion associated with the first outer end, and retraction of a second portion of the actuation member is configured to retract the sleeve portion associated with the second outer end. In other words, the outer ends of the prosthesis may be expanded simultaneously or in sequence. The sleeve 30 can be removed from the first outer end 18 of the prosthesis, such as described herein, while inserted within the vessel portion 220A. For example, the retraction member can be retracted in order to peel or split the removable sleeve 30 and remove it from the first outer end 18 of the prosthesis to allow for expansion thereof.

In one example, FIG. 5B shows the actuation member 108 in a first position. Each of the retraction members, such as the retractions members 46C, 46D of the sleeve 30 is shown gathered at the middle and positioned through the guiding element 135, along the handle 101, and extending through the retaining member 120 so that the enlarged ends 48 are engaged with the retaining member 120. This orientation puts the system 10 at the distal end of the tool 100 such that the tip 106 is contacted with the system 10 at approximately the center. The tip 106 can apply a force at approximately the center of the system 10 suitable to retain the system 10 in a substantially fixed position relative to the tool 100 as the actuation member 108 is moved relative to the system 10. The tool 100 can be attached to the system 10 before entry of the system 10 within the body, and is inserted within the end opening 225 of at least one, if not both, body vessel portions 220A, 220B. Alternatively, the system 10, without the tool 100, may first be inserted into the end opening of at least one, if not both, body vessel portions in a manner such that the retraction members can extend outward through the trauma pathway. Here, the retraction members can then be coupled to the tool 100 as described herein.

According to FIG. 5B, the system 10 and the prosthesis 15 can then be manipulated in order to introduce the second outer end 19 of the prosthesis 15 into the vessel portion 220B through the end opening by a sufficient distance to allow the anchoring members of the prosthesis to engage within the tissue. It can be appreciated that the second outer end 19 of the prosthesis may be inserted into the vessel portion 220B prior to, or subsequent to, the removal of the sleeve 30 from the first outer end 18. The vessel portion 220B may be manually pulled over the second outer end 19 of the prosthesis 15. The sleeve 30 can be removed from the second outer end 19 of the prosthesis, such as described herein, while inserted within the vessel portion 220B to allow for expansion thereof. The vessel portions 220A, 220B can now be sealably engaged to the first and second outer ends 18, 19 of the prosthesis 15.

Figure 5C:
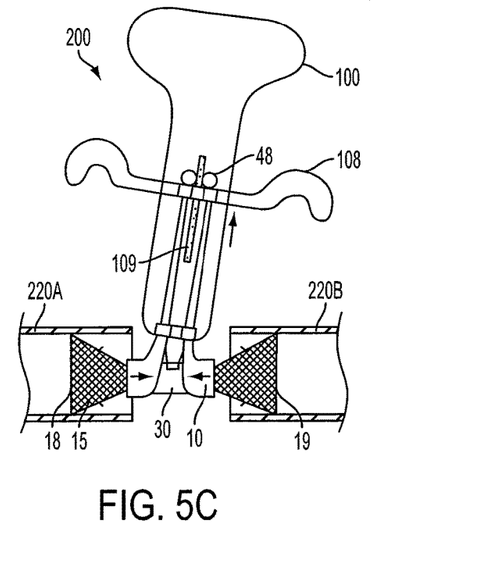
Figure 5D:
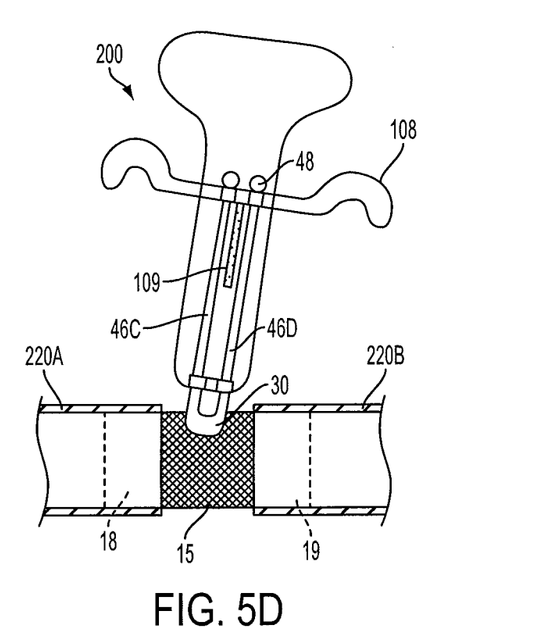
Figure 5E:
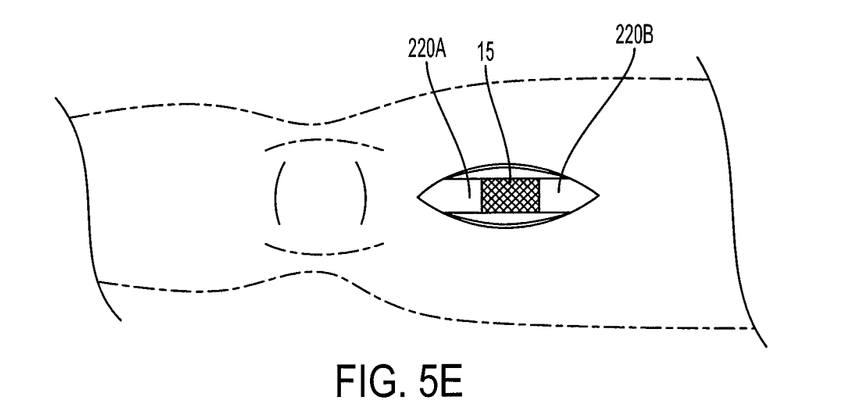

In FIG. 5C, after insertion of both outer ends 18, 19 of the prosthesis 15 into the respective portions 220A, 220B, the actuation member 108 can be moved relative to the prosthesis, such as, e.g., within the slot 109 from the first position toward the second position. As a result, the retraction members can be moved relative to prosthesis to peel or split the sleeve 30. This action removes a portion of the sleeve 30 from the respective outer ends 18, 19 in order to allow for radial expansion of the prosthesis 15 at its outer ends. According to FIG. 5D, the actuation member 108 is in the second position. At this position, the retraction members 46C, 46B and the sleeve 30 can be further moved relative to the prosthesis 15 such that the sleeve 30 is entirely removed from the prosthesis. The radial expansion forces of the prosthesis may aid in the splitting of the sleeve. After full radial expansion of the prosthesis, the system and the sleeve together may be removed from the body. Accordingly, the prosthesis 15 is fully deployed to interconnect the first and second vessel portions 220A, 220B of the body vessel 220 to form a conduit for blood flow. The sutures can then be removed. Preferably, portions of the exterior surfaces of the prosthesis sealably engage with the luminal walls of the body vessel to inhibit leakage of blood and to force blood to flow throughout the body vessel during emergency surgery, and particularly to obtain hemostasis or fluid stability while maintaining blood or fluid perfusion. FIG. 5E shows the prosthesis 15 deployed and interconnecting body vessel portions 220A, 220B within the leg of the patient. Prosthesis 15 can be adapted for permanently placement within the patient, thereby obviating a need for subsequent surgical intervention.

Instead of transecting the vessel, the prosthesis and the distal end of the handle can be manipulated in a laceration or opening formed in the wall of the body vessel. The prosthesis may then be repositioned at a desired location with the body vessel. The prosthesis can be expanded with the assembly 200 such as described herein. Alternatively, the system 10 without the tool 100 can be used to deploy a prosthesis. The clinician would grasp the ends of the retraction member subsequent to positioning within the body vessel portions, and retract the retraction member ends relative to the prosthesis to allow for expansion of the outer ends of the prosthesis.

Figure 6A:
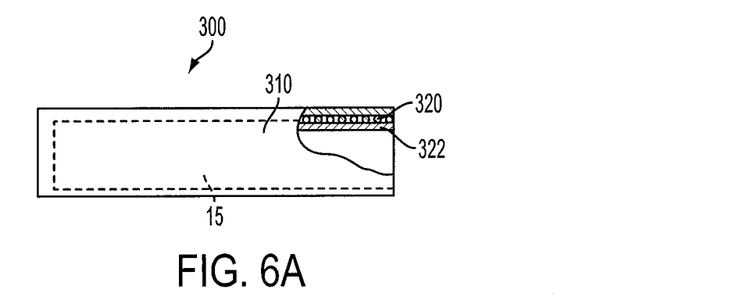
FIG. 6A is an elevation view of another delivery system for deploying a prosthesis, depicting a removable sleeve that can dissolve.

FIGS. 6A-6E illustrate an alternative system 300 and delivery method. FIG. 6A depicts the system 300 including a prosthesis 15 retained in a radially compressed configuration within a removable sleeve 310. A partial cutaway of FIG. 6A shows the various layers of the prosthesis 15, such as a support structure 320 and a graft body 322 in relation to the sleeve 310. To remove the sleeve, the sleeve 310 can be configured to rapidly weaken, and preferably dissolve entirely, in response to application of an activation agent 330 to such configured sleeve. In other words, the sleeve 310 can be weakened to a degree where the radial expansion forces of the prosthesis can overcome the retaining forces of the sleeve, thereby allowing the prosthesis to move to the radially expanded configuration. Thereafter, the 310 sleeve may continue to dissolve in its entirety. In another example, the sleeve can have perforations. The number, shape, and size of the perforations can be selected for a desired dissolution rate. For example, a sleeve with more perforations can dissolve at a faster rate than the same sleeve with fewer perforations. The perforations may also allow for improved surface area contact, and anchoring, when the prosthesis is expanded in the middle of the dissolution process of the sleeve.

One example of an activation agent 330 is saline, which is commonly found in the emergency room setting. Materials of the sleeve 310 that dissolve once interfaced with saline include: pullulan which is an extracellular bacterial polysaccharide produced from starch by *Aureobasidium pullulans*; hydroxypropyl methyl cellulose; non animal-derived film-forming polymers, for example, polyvinyl alcohol, plant-derived film-forming polymers such as starch, starch derivatives, cellulose, celluloses derivatives other than the HPMC as defined herein and mixtures thereof; bacterial-derived film-forming polymers such as exo-polysaccharides like xanthan, acetan, gellan, welan, rhamsan, furcelleran, succinoglycan, scleroglycan, schizophyllan, tamarind gum, curdlan, dextran and mixtures thereof; and gelling systems including one or more cations and/or one or more gelling agents, with cations such as $K^+$, $Na^+$, $Li^+$, $NH_4^+$, $Ca^{++}$, $Mg^{++}$ and mixtures thereof, and gelling agent(s) such as hydrocolloids such as alginates, agar gum, guar gum, locust bean gum (carob), carrageenans, tara gum, gum arabic, ghatti gum, khaya grandifolia gum, tragacanth gum, karaya gum, pectin, arabian (araban), xanthan, gellan gum, konjac mannan, galactomannan, funoran, and mixtures thereof. It can be appreciated by those skilled in the art that other activation agents and corresponding sleeve materials can be selected to perform the same function. Other examples include poly ethylene glycol, poly ethylene oxide, poly vinylpyrrolidone, a glycosaminoglycan, polysaccharides, polysaccharide derivatives, poly hyaluronic acid, poly alginic acid, chitin, chitosan, chitosan derivatives, hydroxyethyl cellulose, hydroxypropyl cellulose, carboxymethyl cellulose, poly peptides, poly lysine, poly glutamic acid, and proteins, such as albumin.

In one example, a polysaccharide may include tamarind gum (such as xyloglucan polymers), guar gum, chitosan, chitosan derivatives, locust bean gum (such as galactomannan polymers), and other industrial gums and polymers, which include, but are not limited to, Tara, Fenugreek, Aloe, Chia, Flaxseed, Psyllium seed, quince seed, xanthan, gellan, welan, rhamsan, dextran, curdlan, pullulan, scleroglucan, schizophyllan, chitin, hydroxyalkyl cellulose, arabinan (such as sugar beets), de-branched arabinan (such as from sugar beets), arabinoxylan (such as rye and wheat flour), galactan (such as from lupin and potatoes), pectic galactan (such as from potatoes), galactomannan (such as from carob, and including both low and high viscosities), glucomannan, lichenan (such as from icelandic moss), mannan (such as ivory nuts), pachyman, rhamnogalacturonan, acacia gum, agar, alginates, carrageenan, chitosan, clavan, hyaluronic acid, heparin, inulin, cellodextrins, and mixtures thereof. Polymers can be crosslinked to improve strength of sleeve and/or solubility of sleeve. Such crosslinking of polymers is described in U.S. Pat. No. 7,960,453, which is incorporated herein by reference in its entirety. While any water-soluble material, such as cellulosic materials, gums, polymers, starches, proteins, and combinations thereof can be used, an example sleeve is made of glucans because of its high water solubility and rapid dissolution. Examples of glucans include pullulan and elsinan. It can be appreciated by those skilled in the art that other activation agents and corresponding sleeve materials can be selected to perform the same function.

The sleeve can be made by the following processes. A solution of the desired sleeve material can be prepared in a water or saline solution. A mandrel can be dipped into the solution to form a dip coating on the mandrel. It is recognized that the sleeve material may be applied by other means to coat the mandrel. Some of the sleeve materials are thermoformable and can be extruded into a tubular segment. Some of the sleeve material can be formed in a sheet that is rolled to form a tubular segment. The coated mandrel can be dried in air to form the sleeve. The prosthesis may be radially compressed with a stent compressor or by other known means in the art. The compressed prosthesis can be transferred to within the lumen of the sleeve.

Figure 6B:
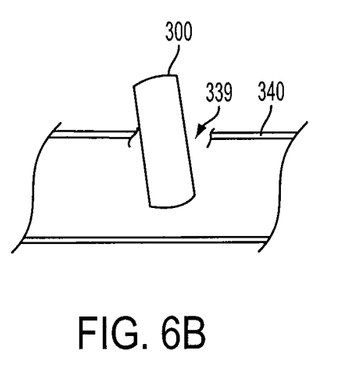
FIGS. 6B-6E are partial elevation cross-sectional views of a damaged body vessel, depicting alternative method steps of deploying a prosthesis using the system of FIG. 6A.
Figure 6C:
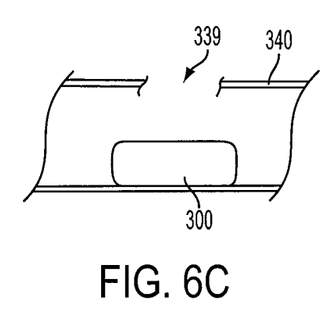
Figure 6D:
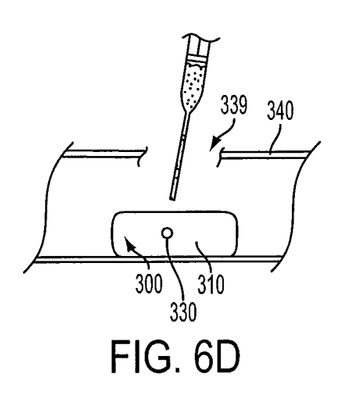
Figure 6E:
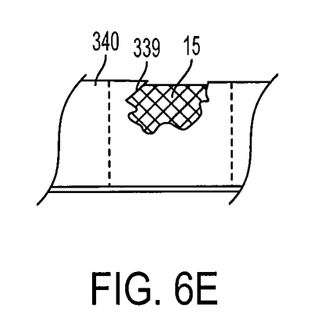

The system 300 can be inserted manually through a laceration 339 of a body vessel 340, as shown in FIG. 6B, and then repositioned to be substantially centered over the laceration, as shown in FIG. 6C. In one example, the system 300 can be inserted into two vessel portions of a transected vessel. The activation agent 330 can be applied to the sleeve 310 in order to begin the weakening or dissolving process. FIG. 6D shows the use of a syringe suitably pressurized to release a sufficient amount of the activation agent 330 to rapidly weaken or dissolve sleeve 310. The time to weaken or dissolve the sleeve 310 can depend on the material and concentration of the sleeve and the activation agent, but it is desirable that the total time be as quick as possible, e.g., less than about 5 to 10 seconds. FIG. 6E shows the prosthesis 15 in the radially expanded configuration engaged with the body vessel 340 after the sleeve 310 has dissolved, sealing the laceration 339 from within or interconnect the two vessel portions, in order to gain hemostasis or fluid stability and still allow blood perfusion or fluid flow.

It can be appreciated by those skilled in the art that specific features of each embodiment of the delivery device are interchangeable among the device embodiments, even where no references to the specific features are made.

Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:

1. A method of open surgical repair of a lacerated or transected body vessel to obtain fluid stability while maintaining fluid flow through the body vessel, comprising:
   inserting a first outer end of a prosthesis into a first vessel portion of the body vessel, wherein the prosthesis comprises a support structure and a graft body, the first outer end of the prosthesis being retained in a compressed configuration with a first sleeve portion, the first outer end being self-expandable and the first sleeve portion being dissolvable;
   inserting a second outer end of the prosthesis into a second vessel portion of the body vessel, wherein the second outer end of the prosthesis is retained in a compressed configuration with a second sleeve portion, the second outer end being self-expandable and the second sleeve portion being dissolvable; and
   dissolving the first and second sleeve portions while the first and second outer ends of the prosthesis are within the first and second vessel portions, the first and second sleeve portions thereby weakening retention of the first and second outer ends and the first and second outer ends radially expanding to engage the first and second vessel portions, the prosthesis comprising a longitudinal length sufficient to bridge and seal the laceration or bridge and interconnect a transected gap between the first and second vessel portions, wherein the first and second sleeve portions dissolve in response to application of an activation agent introduced into the body vessel through the laceration or transection.

2. The method of claim 1, wherein the activation agent is saline.

3. The method of claim 1, wherein the activation agent is applied to the first and second sleeve portions with a syringe.

4. The method of claim 1, wherein the first and second sleeve portions dissolve within 10 seconds of applying the activation agent.

5. The method of claim 1, wherein the first and second sleeve portions dissolve within 5 seconds of applying the activation agent.

6. The method of claim 1, wherein the support structure is a stent pattern.

7. The method of claim 1, wherein the first and second outer ends of the prosthesis each comprise anchor members to engage tissue of the body vessel to fix the first and second outer ends to the first and second vessel portions.

8. The method of claim 1, wherein the first and second sleeves are made of polysaccharide or a derivative thereof.

9. The method of claim 1, wherein the first and second sleeves are made of cellulose or a derivative thereof.

10. The method of claim 1, wherein the first and second sleeves are made of hydroxypropyl methyl cellulose.

11. The method of claim 1, wherein the body vessel is transected, the prosthesis being inserted into the first and second vessel portions through the transected gap between the first and second vessel portions.

12. The method of claim 1, wherein the body vessel is lacerated, the prosthesis being inserted into the first and second vessel portions through the laceration.

13. The method of claim 1, wherein the prosthesis is implanted permanently in the body vessel thereby obviating further surgical intervention or repair.

14. The method of claim 1, wherein the body vessel is a blood vessel.

15. The method of claim 1, wherein the open surgical repair is of a traumatic injury resulting from a gunshot, knife wound, motor vehicle accident, explosion, etc.

16. The method of claim 1, further comprising clamping the first and second vessel portions to restrict fluid flow prior to inserting the first and second outer ends of the prosthesis.

17. The method of claim 1, further comprising fixing the first and second vessel portions in place and keeping end openings thereof opened with sutures or forceps to facilitate inserting the first and second outer ends of the prosthesis.

18. The method of claim 17, wherein triangulated sutures are used to fix the first and second vessel portions in place and keep the end openings opened during insertion of the first and second outer ends of the prosthesis.

19. The method of claim 1, wherein the support structure is a stent pattern, the first and second outer ends of the prosthesis each comprise anchor members to engage tissue of the body vessel to fix the first and second outer ends to the first and second vessel portions, the body vessel is a blood vessel, and the open surgical repair is of a traumatic injury resulting from a gunshot, knife wound, motor vehicle accident, explosion, etc.

20. The method of claim 19, further comprising clamping the first and second vessel portions to restrict fluid flow prior to inserting the first and second outer ends of the prosthesis, and fixing the first and second vessel portions in place and keeping end openings thereof opened with sutures or forceps to facilitate inserting the first and second outer ends of the prosthesis.

21. The method of claim 20, wherein triangulated sutures are used to fix the first and second vessel portions in place and keep the end openings opened during insertion of the first and second outer ends of the prosthesis.

22. The method of claim 21, wherein the first vessel portion is a non-blood supplying vessel end and the second vessel portion is a blood supplying vessel end, the first outer end of the prosthesis being inserted into the first vessel portion before the second outer end of the prosthesis is inserted into the second vessel portion.

23. The method of claim 22, wherein the prosthesis is implanted permanently in the body vessel thereby obviating further surgical intervention or repair.

24. The method of claim 23, wherein the first and second sleeves are made of cellulose or a derivative thereof.

25. The method of claim 24, wherein the first and second sleeves are made of hydroxypropyl methyl cellulose.

26. The method of claim 19, wherein the first and second sleeves are made of cellulose or a derivative thereof.

27. The method of claim 19, wherein the first and second sleeves are made of hydroxypropyl methyl cellulose.

28. The method of claim 19, wherein the first and second sleeve portions dissolve within 10 seconds of applying the activation agent.

29. A method of open surgical repair of a lacerated or transected body vessel to obtain fluid stability while maintaining fluid flow through the body vessel, comprising:
   inserting a first outer end of a prosthesis into a first vessel portion of the body vessel, wherein the prosthesis comprises a support structure and a graft body, the first outer end of the prosthesis being retained in a compressed configuration with a first sleeve portion, the first outer end being self-expandable and the first sleeve portion being dissolvable;
   inserting a second outer end of the prosthesis into a second vessel portion of the body vessel, wherein the second outer end of the prosthesis is retained in a compressed configuration with a second sleeve portion, the second outer end being self-expandable and the second sleeve portion being dissolvable; and
   dissolving the first and second sleeve portions while the first and second outer ends of the prosthesis are within the first and second vessel portions, the first and second sleeve portions thereby weakening retention of the first and second outer ends and the first and second outer ends radially expanding to engage the first and second vessel portions, the prosthesis comprising a longitudinal length sufficient to bridge and seal the laceration or bridge and interconnect a transected gap between the first and second vessel portions, and wherein the first and second sleeve portions dissolve in response to application of an activation agent introduced into the body vessel through the laceration or transection.

30. The method of claim 29, wherein the activation agent is saline.

31. The method of claim 30, wherein the activation agent is applied to the first and second sleeve portions with a syringe.

32. The method of claim 31, wherein the first and second sleeve portions dissolve within 5 seconds of applying the activation agent.

33. The method of claim 29, wherein the first and second sleeves are made of hydroxypropyl methyl cellulose.

* * * * *